US009591996B2

(12) United States Patent
Chang et al.

(10) Patent No.: US 9,591,996 B2
(45) Date of Patent: Mar. 14, 2017

(54) SYSTEM AND METHOD FOR DETECTING TRANSITIONS BETWEEN SITTING AND STANDING STATES

(71) Applicant: LUMO BodyTech, Inc., Palo Alto, CA (US)

(72) Inventors: Andrew Robert Chang, Sunnyvale, CA (US); Andreas Martin Hauenstein, San Mateo, CA (US)

(73) Assignee: Lumo BodyTech, Inc, Mountain View, CA (US)

( * ) Notice: Subject to any disclaimer, the term of this patent is extended or adjusted under 35 U.S.C. 154(b) by 106 days.

(21) Appl. No.: 13/912,999

(22) Filed: Jun. 7, 2013

(65) Prior Publication Data
US 2014/0364769 A1 Dec. 11, 2014

(51) Int. Cl.
*A61B 5/103* (2006.01)
*A61B 5/11* (2006.01)
*A61B 5/00* (2006.01)

(52) U.S. Cl.
CPC .......... *A61B 5/1116* (2013.01); *A61B 5/1126* (2013.01); *A61B 5/6814* (2013.01); *A61B 5/6822* (2013.01); *A61B 5/6823* (2013.01)

(58) Field of Classification Search
None
See application file for complete search history.

(56) References Cited

U.S. PATENT DOCUMENTS 4,633,094 A 12/1986 Knudsen
5,143,088 A 9/1992 Marras et al.
5,158,089 A 10/1992 Swezey et al.
(Continued)

FOREIGN PATENT DOCUMENTS

WO WO 2011064705 A1 * 6/2011 .......... A61B 5/1117
WO WO 2011133799 A1 * 10/2011
WO WO 2013024461 A1 * 2/2013

OTHER PUBLICATIONS

Clifford, Michelle and Gomez, Leticia (2005), "Measuring Tilt with Low-g Accelerometers", in Freescale Semiconductor Application Note, (accessible at http://wvvw.freescale.com/files/sensors/doc/app_note/AN3107.pdf), pp. 01-8.
(Continued)

*Primary Examiner* — Devin Henson
*Assistant Examiner* — Matthew Kremer
(74) *Attorney, Agent, or Firm* — Brian Van Osdol

(57) ABSTRACT

A system and method are described herein for detecting a user's transition between sitting and standing postures. Transitions between sitting and standing states are reliably detected using an accelerometer attached to the user. By modeling error introduced by the accelerometer, and correcting for this error, transitions between sitting and standing states are reliably detected. A microprocessor coupled to the accelerometer converts the captured accelerometer data to approximate vertical acceleration. Vertical velocity, which includes accelerometer error, is determined from the approximate vertical acceleration. The vertical velocity is corrected, and the corrected vertical velocity used to determine vertical displacement. Transitions between sitting and standing states are determined from the vertical displacement.

12 Claims, 7 Drawing Sheets

(56) References Cited

U.S. PATENT DOCUMENTS

| | | | |
|---|---|---|---|
| 5,388,591 A | 2/1995 | Luca et al. | |
| 5,398,697 A | 3/1995 | Spielman | |
| 5,749,838 A | 5/1998 | Kline | |
| 5,916,181 A | 6/1999 | Socci et al. | |
| 5,919,149 A | 7/1999 | Allum | |
| 6,032,530 A | 3/2000 | Hock | |
| 7,264,554 B2 | 9/2007 | Bentley | |
| 7,431,703 B2 | 10/2008 | Salvi et al. | |
| 7,602,301 B1 | 10/2009 | Stirling et al. | |
| 7,634,379 B2 | 12/2009 | Noble | |
| 7,698,830 B2 | 4/2010 | Townsend et al. | |
| 8,206,325 B1 | 6/2012 | Najafi et al. | |
| 8,408,041 B2 | 4/2013 | Ten Kate | |
| 8,749,391 B2 | 6/2014 | Flinsenberg | |
| 8,773,256 B2 | 7/2014 | Ten Kate | |
| 8,928,484 B2 | 1/2015 | Chang et al. | |
| 9,011,352 B2 | 4/2015 | Ten Kate | |
| 9,128,521 B2 | 9/2015 | Chang et al. | |
| 9,286,782 B2 | 3/2016 | Chang et al. | |
| 2003/0050546 A1* | 3/2003 | Desai et al. | 600/347 |
| 2004/0015103 A1 | 1/2004 | Aminian et al. | |
| 2005/0126026 A1 | 6/2005 | Townsend et al. | |
| 2007/0015611 A1 | 1/2007 | Noble et al. | |
| 2007/0118056 A1 | 5/2007 | Wang et al. | |
| 2007/0167671 A1 | 7/2007 | Miller | |
| 2008/0319352 A1 | 12/2008 | Chow et al. | |
| 2009/0069722 A1 | 3/2009 | Flaction et al. | |
| 2009/0312973 A1 | 12/2009 | Hatlestad et al. | |
| 2010/0056943 A1* | 3/2010 | Storm | 600/547 |
| 2010/0152622 A1* | 6/2010 | Teulings | A61B 5/1101 600/595 |
| 2010/0205541 A1 | 8/2010 | Rapaport et al. | |
| 2010/0211349 A1 | 8/2010 | Flaction et al. | |
| 2010/0298655 A1 | 11/2010 | McCombie et al. | |
| 2010/0312152 A1 | 12/2010 | Sarkodie-Gyan et al. | |
| 2010/0317489 A1 | 12/2010 | Flaction | |
| 2011/0063114 A1 | 3/2011 | Ikoyan | |
| 2011/0172951 A1 | 7/2011 | Schlumbohm | |
| 2011/0207581 A1 | 8/2011 | Flaction | |
| 2011/0264325 A1* | 10/2011 | McLaughlin et al. | 701/35 |
| 2012/0016624 A1* | 1/2012 | Caritu | A61B 5/1123 702/141 |
| 2013/0158365 A1* | 6/2013 | Chey et al. | 600/301 |
| 2013/0190657 A1 | 7/2013 | Flaction et al. | |
| 2013/0190658 A1 | 7/2013 | Flaction et al. | |
| 2014/0277633 A1 | 9/2014 | Flaction | |
| 2016/0051858 A1 | 2/2016 | Flaction et al. | |

OTHER PUBLICATIONS

Kesson, Malcolm (2002), "Mel. Align Y Axis to Vector", in CG References & Tutorials at Fundza.com (accessible at http://www.fundza.com/mel/axis_to_vector/align_axis_to_vector.html), pp. 1-6.

Patel, A.T. and Ogle, Abna A. (2000), "Diagnosis and Management of Acute Low Back Pain", in American Family Physician 15:61 (6) (accessible at http://aafp.org/afp/2000/0315/p1779.html), pp. 1779-1786.

Unknown (2000), "Information from Your Family Doctor Acule Low Back Pain", in American Family Physic1an 15 51 (6} (accessible at http://www.aafp.org/afp/2000/0315/p1789 html), pp. 1~4.

Unknown, "Accelerometer", in Wikipedia (archived Apr. 1, 2011 at http:i/web archive.org/V\leb/2011 0401205940/http://en.wikipedia.org/wiki/Accelerometer), pp. 1-21.

Unknown, "Back Pain", in Wikipedia (archived Feb. 25, 2011 at http:l/web.archive.org/web/20110225132'125/ 0http://en.wikipedia.orgiwiki/Back~pain) . . . pp. 1-22.

Unknown, "Mahalanobis Distance", in Wikipedia (ardlived Mar. 29, 2010 at http://web.archive.orft!/ 0 webi201 00329232341/http:/len.wikipedia.org.l'<>viki/Mahalanobis_distance), pp. 1-8.

Unknown, "Rotation", in Wikipedia (archived I'vlarch 31, 2011 at http://web archive.org/web/20110331232736/http://en.wikipedia.org/wiki/Rotation), pp. 1-13.

Unknown, "A Patient's Guide to Rehabilitation for Low Back Pain", University of Maryland Spine Program (archived 8 Jun. 7, 2011 at http://web.archive.org/web/20110607181952/http://www.umm.edu/spinecenter/education/rehabilitation_for_low_back_pain.htm). pp. 1-10.

Unknown, "Sensors", at freescale.com (accessed May 14, 2012 at http://www.freescale.com/webapp/sps/site/homepage.jsp?nodel=011269). pp. 1-2.

Unknown, "Neutral Spine", in Wikipedia (archived Feb. 12, 2011 at http://web.archive.org/web/20110212145135/http://en.wikipedia.orglwiki/Neutral_spine), pp. 1-7.

* cited by examiner

SYSTEM AND METHOD FOR DETECTING TRANSITIONS BETWEEN SITTING AND STANDING STATES

BACKGROUND OF THE INVENTION

Field of the Invention

The present invention relates generally to biomechanical sensors used for biofeedback, to biomechanical sensors that interface with computing devices, and to detecting transitions between sitting and standing states using such devices attached to a user.

Description of the Prior Art

Monitoring and tracking posture, postural changes, and activity of a user presents many challenges. One system for monitoring and tracking posture, postural changes, and activity uses a sensor attached to the user to collect data. The sensor produces a stream of three-dimensional data which is processed by a microprocessor.

A challenge in such a system is detecting transitions between sitting and standing states; the user moving from standing to sitting, or the user moving from sitting to standing. Information on whether the user is sitting or standing is needed, for example, to collect reliable statistics about the time the user spends sitting versus the time the user spends standing. Transitions between sitting and standing states must be detected to collect these statistics.

One type of sensor attached to the user to detect such transitions, as well as to track posture, postural changes, and user activity is an accelerometer which measures acceleration of the user in three orthogonal axes: y (up and down), z (forward and backward), and x (side to side). The accelerometer is attached to the user, for example as a belt attaching the accelerometer along the spine, a pendant or necklace attaching the accelerometer along the sternum or chest, or using other means of attaching the accelerometer to the user's torso, head, or neck. Particularly when attached to the user along the spine or torso, the accelerometer is in almost the same orientation when the user is sitting as when the user is standing.

This means a transition between sitting and standing states cannot be detected by simply examining or comparing data from the accelerometer for example when the user is sitting and when the user is standing. Rather, the transition must be detected by analyzing the motion of the user as reported by the accelerometer during the movement from sitting to standing states, or from standing to sitting states.

On initial examination, the problem of detecting transitions between sitting and standing states using data from an accelerometer seems simple.

The output of the accelerometer at any point in time is a combination of two sets of forces: an acceleration due to gravity, and an acceleration due to user motion. Since the acceleration due to gravity is a constant, it should be possible to separate out the acceleration due to gravity, leaving the acceleration due to user motion.

Then, as taught by basic physics, the vertical velocity of the accelerometer over time is calculated from the acceleration due to user motion over time, and similarly the vertical distance the user moved over time is calculated from the vertical velocity over time. Using the vertical distance the user moved over time to detect vertical displacement, that is, changes in the up and down y distance over time, we can detect when the user transitions from the standing to sitting state, as y goes down a small amount, and when the user transitions from the sitting to standing state, with y going up a small amount. Conceptually this process seems simple.

But producing vertical distance over time using only data from an accelerometer in the real world is a problem with many challenges. One challenge is that accelerometers introduce errors into the acceleration data, including noise, offset errors, and scaling errors. These errors change with environmental factors such as temperature, change over time, and are different with respect to each axis measured. Errors in the acceleration data are magnified by the process of converting acceleration to velocity and then to distance, resulting in errors which increase over time as distance is determined.

Another challenge is separating acceleration due to gravity from acceleration due to user motion. One approach commonly used in other contexts, known as frequency analysis, is not applicable to detecting changes from sitting to standing and vice versa.

Another approach to separating acceleration due to gravity from acceleration due to user motion is to incorporate additional data from another type of sensor such as a gyroscope. Data from the gyroscope is used to compute angular data. This additional angular data simplifies the process of separating accelerometer data into acceleration due to gravity and acceleration due to user motion.

But gyroscopes introduce their own set of challenges, including the electrical power needed to run them, and more important, the computational power required to combine the output of the gyroscope with the output of the accelerometer. For the scale of small battery-operated devices meant to be worn inconspicuously by the user, the amount of computational power required to incorporate data from a gyroscope is relatively large. Such amounts of computational power require large amounts of electrical energy, which means either large batteries, or short battery life with frequent recharging, neither of which are desirable in a small, portable, consumer device.

These challenges introduced by using a gyroscope in addition to an accelerometer are easily avoided by not using a gyroscope. But that brings back the problem of detecting transitions between sitting and standing states using only an accelerometer, with its inherent sources of error.

What is needed is a method for detecting transitions between sitting and standing states, using an accelerometer attached to the user.

SUMMARY

In an embodiment is a method of detecting a user transition between sitting and standing states comprising: capturing, by a tri-axial accelerometer attached to a user, a plurality of points of accelerometer data over a period of time, determining, by a microprocessor, a plurality of points of approximate vertical acceleration due to user motion from the plurality of points of accelerometer data over a period of time, determining, by the microprocessor, a plurality of points of vertical velocity from the plurality of points of approximate vertical acceleration due to user motion, segmenting, by the microprocessor, the plurality of points of vertical velocity, correcting, by the microprocessor, each of the segments of points of vertical velocity, determining, by the microprocessor, segments of points of vertical displacement from the corrected segments of points of vertical velocity, and detecting, by the microprocessor, a user transition between sitting and standing states from the segments of points of vertical displacement.

In an embodiment the method of segmenting the plurality of points of vertical velocity comprises: selecting, by the microprocessor, a first point of the plurality of points of vertical velocity as a beginning of a segment, and selecting, by the microprocessor, a second point of the plurality of points of vertical velocity as an end of the segment, wherein the segment contains a number of points of the plurality of points of vertical velocity, and determining that a minimal amount of user motion is present at the first and second points.

In an embodiment the method of correcting each of the segments of points of vertical velocity comprises: determining, by the microprocessor, a linear error for each of the segments of points of vertical velocity, and removing, by the microprocessor, the linear error from each of the segments of points of vertical velocity.

In an embodiment the method of determining that a minimal amount of user motion is present at the first and second points comprises, for each of the first and second points: setting a motion threshold to be a first predetermined value if a user motion at the point is less than a predetermined motion limit, setting the motion threshold to be a second predetermined value if the user motion at the point is greater than or equal to the predetermined motion limit, and determining that a degree of user motion over a neighboring period of time ending at the point is less than the set motion threshold.

In an embodiment is an apparatus for detecting a user transition between sitting and standing states comprising: a tri-axial accelerometer attached to a user configured to capture a plurality of points of accelerometer data over a period of time, and a microprocessor, coupled to the tri-axial accelerometer, the microprocessor configured to: determine a plurality of points of approximate vertical acceleration due to user motion from the plurality of points of accelerometer data, determine a plurality of points of vertical velocity from the plurality of points of approximate vertical acceleration due to user motion, segment the plurality of points of vertical velocity, correct each of the segments of points of vertical velocity, determine segments of points of vertical displacement from the corrected segments of points of vertical velocity, and detect a user transition between sitting and standing states from the segments of points of vertical displacement.

In an embodiment is an apparatus where the microprocessor is configured to segment the plurality of points of vertical velocity by being configured to: select a first point of the plurality of points of vertical velocity as a beginning of a segment, and select a second point of the plurality of points of vertical velocity as an end of the segment, wherein the segment contains a number of points of the plurality of points of vertical velocity, and determine that a minimal amount of user motion is present at the first and second points.

In an embodiment is an apparatus where the microprocessor is configured to determine that a minimal amount of user motion is present at the first and second points by being configured to, for each of the first and second points: set a motion threshold to be a first predetermined value if a user motion at the point is less than a predetermined motion limit, set the motion threshold to be a second predetermined value if the user motion at the point is greater than or equal to the predetermined motion limit, and determine that a degree of user motion over a neighboring period of time ending at the point is less than the set motion threshold.

In an embodiment is an apparatus where the microprocessor is configured to correct the segments of points of vertical velocity by being configured to: determine a linear error for each segment of points of vertical velocity, and remove the linear error from each segment of points of vertical velocity.

In an embodiment is a non-transitory computer readable medium having stored thereupon computing instructions comprising: a code segment to capture from a tri-axial accelerometer attached to a user a plurality of points of accelerometer data over a period of time, a code segment to determine a plurality of points of approximate vertical acceleration due to user motion from the plurality of points of accelerometer data over a period of time, a code segment to determine a plurality of points of vertical velocity from the plurality of points of approximate vertical acceleration due to user motion, a code segment to segment the plurality of points of vertical velocity, a code segment to correct each of the segments of points of vertical velocity, a code segment to determine segments of points of vertical displacement from the corrected segments of points of vertical velocity, and a code segment to detect a user transition between sitting and standing states from the segments of points of vertical displacement.

In an embodiment is a non-transitory computer readable medium where the code segment to segment the plurality of points of vertical velocity further comprises: a code segment to select a first point of the plurality of points of vertical velocity as a beginning of a segment, and to select a second point of the plurality of points of vertical velocity as an end of the segment, wherein the segment contains a number of points of the plurality of points of vertical velocity, and determine that a minimal amount of user motion is present at the first and second points.

In an embodiment is a non-transitory computer readable medium where the code segment to determine that a minimal amount of user motion is present at the first and second points further comprises a code segment to, for each of the first and second points: set a motion threshold to be a first predetermined value if a user motion at the point is less than a predetermined motion limit, set the motion threshold to be a second predetermined value if the user motion at the point is greater than or equal to the predetermined motion limit, and determine that a degree of user motion over a neighboring period of time ending at the point is less than the set motion threshold.

In an embodiment is a non-transitory computer readable medium where the code segment to correct the segments of points of vertical velocity further comprises: a code segment to determine a linear error for each segment of points of vertical velocity, and a code segment to remove the linear error from each segment of points of vertical velocity.

DETAILED DESCRIPTION OF THE INVENTION

Figure 1:
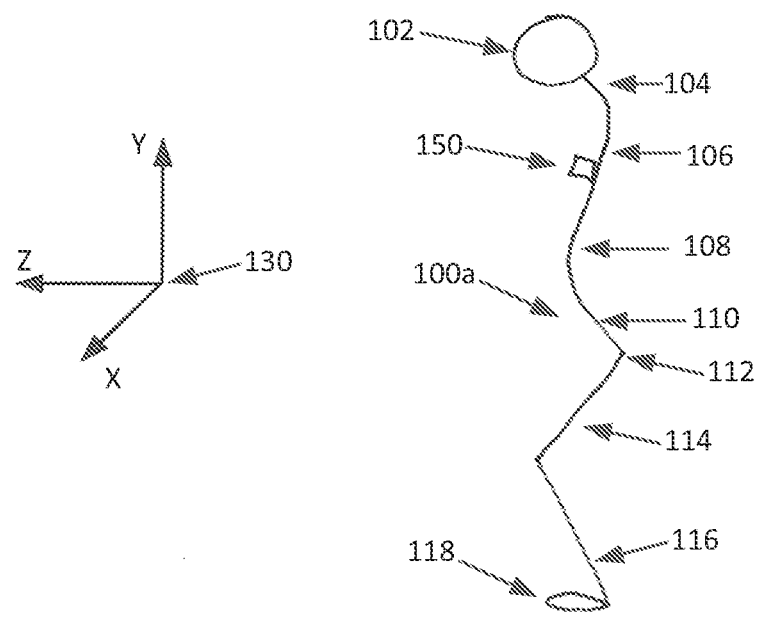
FIG. 1 is a diagram illustrating user posture in standing and sitting states.
Figure 1:
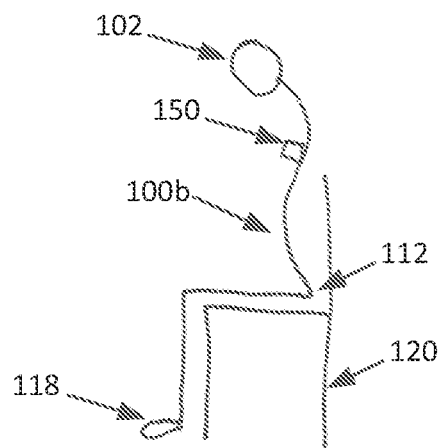

Presented herein are various embodiments of a sensor device and methods for using the sensor device to detect a transition between sitting and standing states.

The sensor device comprises a tri-axial accelerometer coupled to a microprocessor which analyzes directional movement data captured by the accelerometer. When the accelerometer is attached to a user, the microprocessor analyzes captured accelerometer data indicative of a user's motion in three dimensions (x, y, z) in real-time to determine a user's movement state (e.g., standing, sitting, lying, running, or walking) and to detect transitions between states, such as detecting transitions between sitting and standing states.

To detect a transition between sitting and standing states, the accelerometer can be attached anywhere on the head or torso of the user, including but not limited to the head or neck, or on the torso such as along the spine, or on the chest or abdomen.

In an embodiment, accelerometer data is captured over time and processed by the microprocessor coupled to the accelerometer. The captured accelerometer data is a composite of two forces: an acceleration due to gravity, and an acceleration due to user motion. While vertical acceleration due to user motion is difficult to determine from accelerometer data alone, an approximation can be used. The magnitude of the accelerometer data is determined; as is known in the art, this is the square root of the sums of the squares of the individual x, y, and z acceleration values. The amount this magnitude differs from the acceleration due to gravity, the excess magnitude, provides a suitable approximation for vertical acceleration due to user motion. Thus, an approximate vertical acceleration due to user motion is determined from the plurality of points of accelerometer data by determining a magnitude of each of the plurality of points of accelerometer data, and subtracting the acceleration due to gravity from the magnitude of each of the plurality of points of accelerometer data.

A running estimate of user vertical motion is determined from the y accelerometer data. This user vertical motion gives an estimate of the user's motion in the y direction at a point in time.

When the user is not moving, the accelerometer data includes only the acceleration due to gravity, and therefore the magnitude of the accelerometer data when the user is not moving should equal the acceleration due to gravity. Therefore, a long-term running average of the magnitude of each of the plurality of points of accelerometer data is maintained and this value is used as the value for the acceleration due to gravity. This long-term running average may include only magnitude samples when user motion is minimal, determined by user vertical motion below a threshold.

Vertical velocity is determined by integrating the approximate vertical acceleration due to user motion. This vertical velocity includes a linear error which increases with time. This linear error in vertical velocity can be determined and corrected.

The vertical velocity is segmented, and each of the segments of points of vertical velocity are corrected by determining a linear error for each of the segments of points of vertical velocity, and removing the linear error from each of the segments of points vertical velocity, thereby determining a corrected segment of points of vertical velocity for each segment of points of vertical velocity.

A segment of points of vertical displacement is determined for each corrected segment of points of vertical velocity.

Transitions between sitting and standing states are determined using the segments of points of vertical displacement. The vertical displacements at the beginning and end of a segment of points of vertical displacement are compared and a change in vertical displacement determined. If the change in vertical displacement is positive and greater than a predefined limit, a transition between sitting and standing states has been detected. If the change in vertical displacement is negative and less than the predefined limit, a transition between standing and sitting states has been detected.

Turning now to FIG. 1, a diagram of a user 100 is shown standing 100a and sitting 100b in a chair 120. This abbreviated and schematic form shows user 100's head 102 and spine, divided into cervical 104, thoracic 106, lumbar 108, and sacral 110 regions as known in the art. Also illustrated are hips 112, upper legs 114, lower legs 116, and feet 118. As known in the art, the torso is an anatomical term referring to the central part of the body from which extend the neck and limbs. As known in the art, anterior refers to the front portion of user 100, and posterior refers to the rear of user 100.

FIG. 1 shows placement of accelerometer 150 on the user's chest, which for example could be in the form of a necklace, a pendant, or a belt or other means securing accelerometer 150 to the user's chest. In other embodiments, to detect a transition between sitting and standing states accelerometer 150 may be placed on the head, neck, or torso, or may be embedded in or attached to clothing worn by the user.

FIG. 1 also shows a representation of the axes of motion sensed by accelerometer 150, with the y axis representing vertical acceleration and motion up and down, the z axis representing horizontal acceleration and motion forward and backward, and the x axis representing horizontal acceleration and motion from side to side.

While an ideal orientation of accelerometer 150 on user 100 would have accelerometer 150 positioned such that the vertical y axis of accelerometer 150 is vertical to the ground, and the horizontal x and z axes of accelerometer 150 are parallel to the ground, such is seldom the case. As is illustrated in FIG. 1, accelerometer 150 as shown is positioned on the chest of user 100 rotated about the x axis.

This orientation error introduces error into the accelerometer data. If, for example, accelerometer 150 is sitting on a flat surface positioned such that the vertical y axis of accelerometer 150 is vertical to the ground, and the horizontal x and z axes of accelerometer 150 are parallel to the ground, the acceleration on the horizontal x and z axes would be zero, and the acceleration on the vertical y axis would be equal to the acceleration due to gravity, g. As an example, if accelerometer 150 is rotated about the x axis, the acceleration due to gravity on the horizontal x axis would still be zero, but the acceleration due to gravity on the horizontal z axis due to gravity would increase, and the acceleration due to gravity on the vertical y axis would decrease. The orientation error is also compounded by the orientation of the user shifting during motion, for example the torso shifting position as the user sits or stands. This orientation error is corrected as described later herein.

Figure 2:
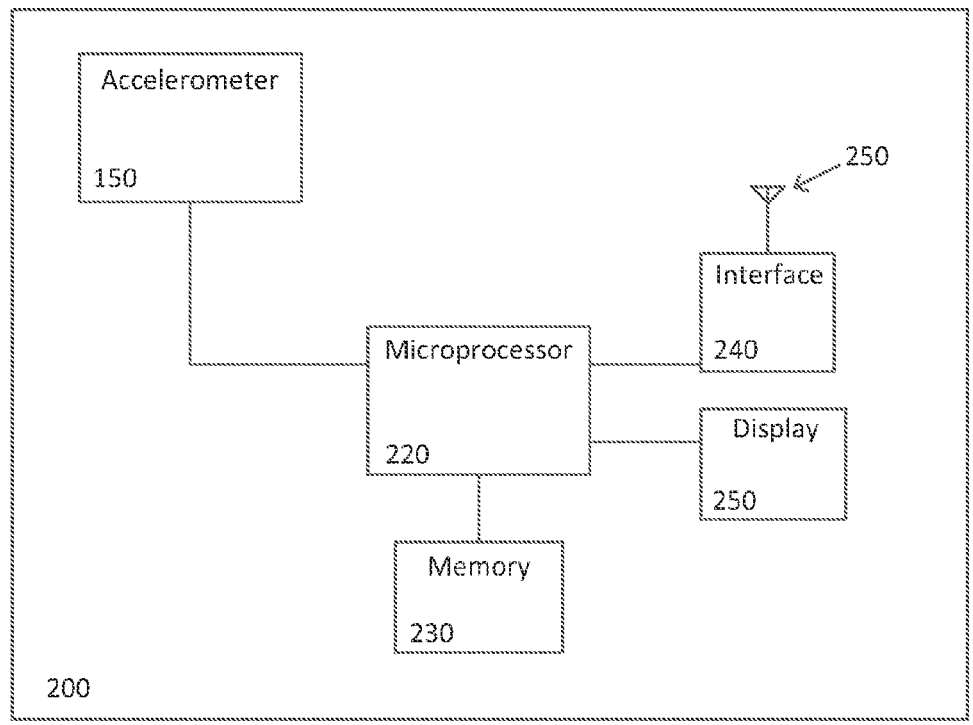
FIG. 2 is a block diagram of a sensor device according to an embodiment.

Turning now to FIG. 2, a block diagram of a sensor device according to an embodiment is shown. Sensor device 200 comprises tri-axial accelerometer 150, which is coupled to a microprocessor 220. Microprocessor 220 is coupled to memory 230, and to optional interfaces 240 and 250. In one embodiment, interface 240 is a wireless interface with antenna 250. Suitable technologies for wireless interface 240 include but are not limited to IEEE 802.15.1 Bluetooth® wireless communications, IEEE 802.15 ZigBee® wireless communications, or IEEE 802.11 Wi-Fi wireless communications. Optional interface 250 can be a visible display such as a light emitting diode (LED) display, organic light emitting diode (OLED) display, liquid crystal display (LCD), or the like. Components and subsystems known in the art such as batteries, charging, and power control are not shown for clarity.

Suitable accelerometers for tri-axial accelerometer 150 are produced by companies such as Analog Devices®, STMicroelectronics®, Freescale® Semiconductor, and others. While these tri-axial accelerometers incorporate three accelerometers mounted mutually orthogonally in one package, three separate accelerometers, mounted mutually orthogonally, may also be used. In an embodiment, a tri-axial accelerometer from STMicroelectronics is used.

It should be noted that while the discussions herein make use of measurements and quantities in meters, meters/sec, meters/sec$^2$ and so on, accelerometers produce data in their own reference system. As an example, the LIS3DH tri-axial accelerometer from STMicroelectronics captures 10-bit accelerometer data with selectable ranges of ±2g, ±4 g, ±8 g, or ±16 g. As is known in the art, results of computation using this captured accelerometer data need only be scaled to familiar units such as meters and meters/sec when such results are presented to a user.

Suitable microprocessors for microprocessor 220 are produced by Intel®, Texas Instruments®, ARM® Ltd, NXP®, and others. In an embodiment a Cortex® M3 microprocessor from NXP is used.

Memory 230 comprises high-speed read-write memory such as random access memory (RAM) or synchronous dynamic random access memory (SDRAM) for storing instructions and data during microprocessor operation, as well as nonvolatile memory such as electrically erasable programmable read only memory (EEPROM) or Flash for storing instructions comprising the operating software of sensor device 200 and its data. It should be noted that memory 230 may be an integral part of microprocessor 220 in a system on a chip (SOC) design, or may be separate components coupled to microprocessor 220. In an embodiment, the Cortex M3 microprocessor includes up to 1 megabyte of non-volatile storage (Flash) and up to 200 thousand bytes of high speed volatile memory (RAM).

Tri-axial accelerometer 150 may be mounted in the same enclosure as microprocessor 220, memory 230, and optional interfaces 240 and 250; or tri-axial accelerometer 150 may be mounted separately from microprocessor 220, memory 230, and optional interfaces 240 and 250 and coupled to microprocessor 220 through wired or wireless means known in the art.

Figure 3:
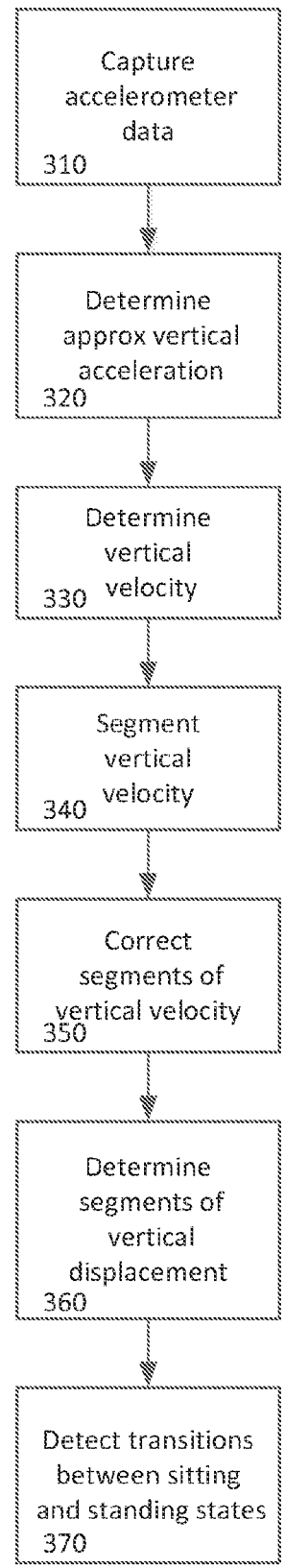
FIG. 3 is a flowchart detailing a method of detecting a transition between sitting and standing states according to an embodiment.

Turning now to FIG. 3, a flowchart detailing a method of detecting a transition between sitting and standing states according to an embodiment is shown.

In step 310, accelerometer data is captured by a tri-axial accelerometer as a series of points over time. This captured accelerometer data represents motion of the user to which the tri-axial accelerometer is attached. In an embodiment, tri-axial accelerometer 150 captures a plurality of points of accelerometer data over time as acceleration data x(t), y(t), z(t) at a periodic sample rate, for example 25 points per second.

In an embodiment, a running determination of user vertical motion is performed with each sample of accelerometer data. This user vertical motion gives an estimate of the user's motion in the y direction at a point in time.

Samples of the y-axis accelerometer data are bandpass filtered over the range 2 to 5 cycles per second (Hertz, Hz). User vertical motion is determined from this bandpass filtered y-axis accelerometer data. This determination of user vertical motion is continuously updated, with each incoming sample of accelerometer data for the y axis, and provides a measure of user vertical motion at a point in time. While a Butterworth filter is used in an embodiment, other filter topologies may also be used.

In step 320, approximate vertical acceleration is determined from the captured accelerometer data. The captured accelerometer data is a composite of two sources of acceleration: the acceleration due to gravity g, and the acceleration due to user motion.

Figure 4:
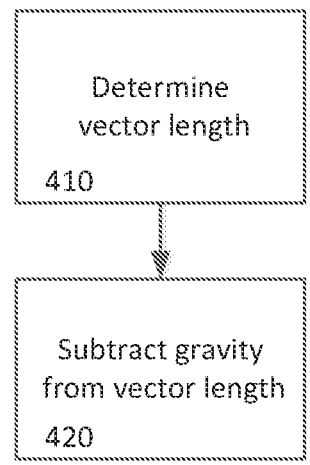
FIG. 4 is a flowchart detailing a method of determining vertical acceleration according to an embodiment.

This process of determining approximate vertical acceleration from accelerometer data is shown in more detail in the flowchart of FIG. 4.

Recall that the captured accelerometer data is a composite of two forces: the acceleration due to gravity, and the acceleration due to user motion.

In step 410, a magnitude is determined by the microprocessor from the captured accelerometer data using the x, y, and z axis components of acceleration at a time t, x(t), y(t), and z(t):

$$\sqrt{x^2(t)+y^2(t)+z^2(t)}$$

By determining the magnitude of the combined horizontal x, vertical y and the forward-backward z acceleration, this computation corrects for orientation errors as shown in FIG. 1, as well as orientation changes for the user leaning forward while transitioning from sitting to standing states, as the computation is insensitive to body position changes.

In step 420, the acceleration due to gravity, g, is subtracted from this magnitude to determine approximate vertical acceleration due to user motion $a_v(t)$ at a time t as:

$$a_v(t) \approx \sqrt{x^2(t)+y^2(t)+z^2(t)} - g$$

In an embodiment, rather than treat the acceleration due to gravity as a constant, the value for the acceleration due to gravity is instead determined by accelerometer data. Using accelerometer data to determine the acceleration due to gravity corrects for certain types of accelerometer error including accelerometer drift over time. It has been observed that over a long period of time, the user to whom the accelerometer is attached is stationary. When the user, and therefore the accelerometer attached to the user is stationary, the magnitude of the acceleration (x, y, z) reported by the accelerometer equals the acceleration due to gravity:

$$\sqrt{x^2+y^2+z^2} = g$$

when stationary

Therefore, in an embodiment, a long-term running average of the magnitude of captured accelerometer data $\sqrt{x^2+y^2+z^2}$ when the user is stationary is maintained and used as the constant for the acceleration due to gravity.

Thus, for each point of captured accelerometer data where the user vertical motion is below a threshold, the running average value of $\tilde{g}$ is determined as:

$$\tilde{g} = \alpha \tilde{g} + (1-\alpha)\sqrt{x^2+y^2+z^2}$$

where in an embodiment α is approximately 0.999, producing a gradual shift. In this long-term running average, each new point of captured accelerometer data only alters the running average g̃ slightly. Periodically, for example once per minute, the value of g used in determining vertical acceleration due to user motion from vertical acceleration in step 320 above is updated with the value of g̃ determined in the running average.

Returning to FIG. 3, now that approximate vertical acceleration due to user motion $a_v(t)$ has been determined from the captured plurality of points of accelerometer data, in step 330 a vertical velocity $v_v(t)$ is determined from the approximate vertical acceleration due to user motion $a_v(t)$. As understood from basic physics, the integral of acceleration is velocity. In an embodiment, numerical integration is used. While many methods of numerical integration are known to the art and may be used, one method of numerical integration is to sum the area of rectangles of height $a_v(t)$ and width Δt, where Δt is the time between samples. The area of such a rectangle is the height times the width: $a_v(t)\Delta t$. By defining Δt=1, the process of numerical integration becomes a summing of the approximate vertical acceleration due to user motion $a_v(t)$ at a time t, such that $$v_v(t) \approx \sum_{i=0}^{t} a_v(i)$$

where $v_v(t)$ is the vertical velocity at a time t, and $a_v(i)$ is the approximate vertical acceleration due to user motion as determined previously.

As is known in the art, real world accelerometers have errors, including but not limited to offset errors, scaling errors, and non-linearity errors. With a tri-axial accelerometer incorporating three accelerometers mounted mutually orthogonally in one package, or an alternate embodiment using three separate accelerometers mounted mutually orthogonally, these errors are present for each accelerometer, and are expected to be different for each axis, and vary with time and environmental conditions such as temperature.

In an embodiment, these errors are addressed by being modeled as a constant which is added to the approximate vertical acceleration due to user motion. Accordingly, rather than just integrating vertical acceleration due to user motion to obtain vertical velocity in step 330, the sum of vertical acceleration due to user motion, plus an error, is integrated, which produces vertical velocity plus a linear error that increases with time:

$$\int (a_v(t)+e)dt = \int a_v(t)dt + \int e\,dt = v_v(t) + et$$

where e represents the error in the vertical acceleration due to user motion.

Examining this equation, consider two points in time, $t_1$ and $t_2$ with $t_2 > t_1$. Assume that the values of velocity at $t_1$ and $t_2$ are the same, that is, $v_v(t_2) = v_v(t_1)$. But from the equation above, because of the linear error:

$$v_v(t_2) = v_v(t_1) + e(t_2-t_1)$$

the linear error $e(t_2-t_1)$ is added to the vertical velocity $v_v(t_2)$ at point $t_2$.

Figure 5:
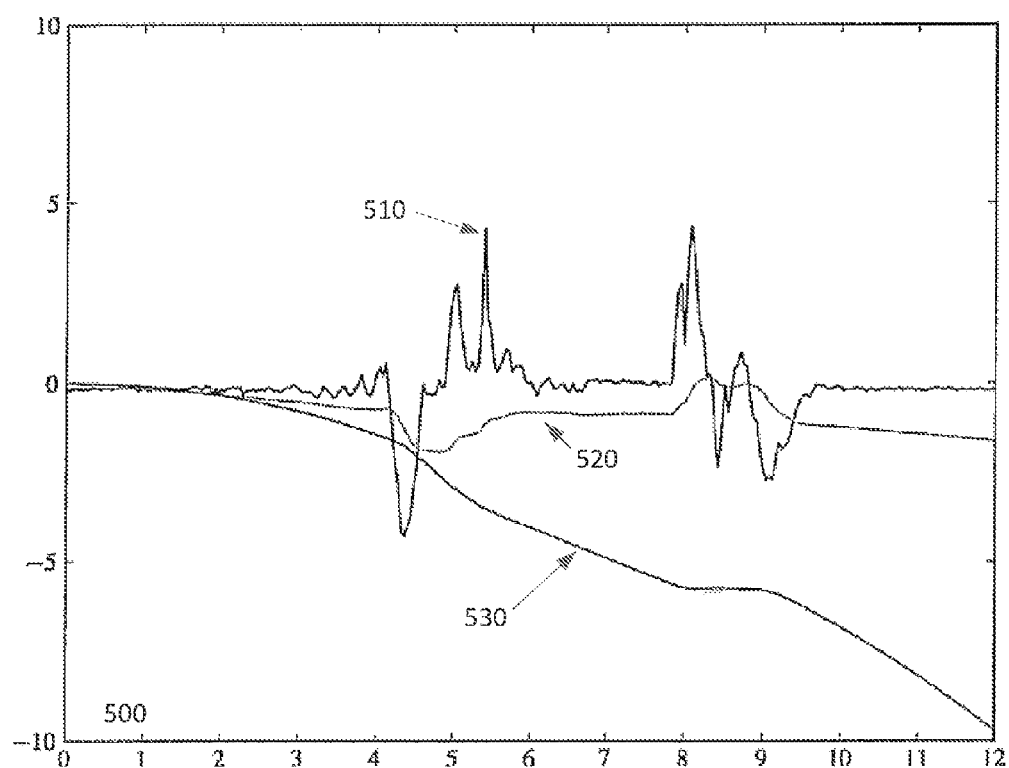
FIG. 5 is a graph of determining vertical displacement from accelerometer data.

The effects of such error is shown in the graph of FIG. 5. Line 510 shows the approximate acceleration due to user motion a(t) over time as captured from the accelerometer attached to the user. Line 520 shows vertical velocity $v_v(t)$ over time, and line 530 shows vertical displacement $s_v(t)$ over time. The horizontal axis is time in seconds; the vertical axis is vertical displacement in meters. The effects of error in the approximate acceleration due to user motion a(t) 510 on vertical velocity $v_v(t)$ are readily apparent. In the interval from zero to three seconds, for example, approximate acceleration due to user motion a(t) 510 is close to zero, yet vertical velocity $v_v(t)$ 520 is drifting negative, and vertical displacement $s_v(t)$ 530 is going increasingly negative. A similar error growth is shown in the interval from ten to twelve seconds, where once again, approximate acceleration due to user motion a(t) 510 is close to zero, yet vertical velocity $v_v(t)$ 520 is drifting increasingly negative, and vertical displacement $s_v(t)$ 530 reaches an alarming value of nearly negative ten meters.

The linear error in the vertical velocity can be corrected. Then, using a corrected vertical velocity to determine a vertical displacement produces an accurate vertical displacement, which can be used for detecting transitions between sitting and standing states.

The correction process determines this linear error in the points of vertical velocity and removes it. In the discussion which follows, reference will be made to the graph of FIG. 6, in which line 510 again shows the approximate acceleration due to user motion a(t) over time as captured from a tri-axial accelerometer attached to the user; this approximate acceleration due to user motion a(t) 510 is the same data as is used in FIG. 5 and the accompanying discussion. Line 620 shows corrected vertical velocity $\tilde{v}_v(t)$ over time, and line 630 shows vertical displacement $s_v(t)$ over time as determined from corrected vertical velocity $\tilde{v}_v(t)$. Segments 640a through 640h shown in the graph as applied to corrected vertical velocity $\tilde{v}_v(t)$ 620 over time, and vertical displacement $s_v(t)$ 630 over time will be discussed further herein. The horizontal axis is time in seconds; the vertical axis is vertical displacement in meters.

The correction process models the errors in the vertical velocity $v_v(t)$ as linear in nature. To correct for this linear error, first the plurality of points of vertical velocity $v_v(t)$ are segmented, for example, into the segments 640a through 640h of FIG. 6. Segments of points of vertical velocity $v_v(t)$ are chosen to include a plurality of points of vertical velocity $v_v(t)$ in a range of time from a minimum to a maximum, for example, from one to five seconds in length.

To understand the correction process, assume beginning and end points for a segment of points of vertical velocity $v_v(t)$ have been chosen. When a user motion of a point is close to zero, the point is considered quiet. When the beginning and end points of the segment are both quiet, the difference in vertical velocity between the beginning point and the end point of the segment is the linear error. A linear equation for a line between the beginning point and the end point of the segment is determined. The value of this equation at each point t in the segment is the linear error at that point. This linear error is subtracted from the vertical velocity $v_v(t)$ to produce a point of corrected vertical velocity $\tilde{v}_v(t)$.

In an embodiment, determining that the user motion at a point is close to zero uses the criteria that the approximate vertical acceleration due to user motion at the point is close to zero.

In another embodiment, determining that the user motion at a point is close to zero uses the criteria that a bumpiness neighboring the point is below a threshold determined by user vertical motion at that point. When the user vertical motion at the point is below a threshold, a low amount of bumpiness is accepted, and when the user vertical motion is above the threshold, a higher amount of bumpiness is accepted.

Returning to the flowchart of FIG. 3, in step 340, the plurality of points of vertical velocity are segmented. Beginning and end points for a segment are chosen, such that:

the length of the segment from $t_1$ and $t_2$ is within predetermined limits:

$$\theta < t_2 - t_1 < \rho, \text{ and}$$

a minimal amount of user motion is present at the beginning and end points.

$\theta$ and $\rho$ determine the minimum and maximum length of a segment, and are selected based on a number of factors such as the sample rate and expected error. In operation, once beginning point $t_1$ is chosen, end point $t_2$ is chosen initially as $t_2=t_1+\theta$. In an embodiment, the limits set by minimum and maximum times $\theta$ and $\rho$ are equal to $\theta=1$ second and $\rho=5$ seconds. In terms of points, at a 25 point per second rate, $\theta=25$ points and $\rho=125$ points.

In an embodiment, once the beginning point $t_1$ has been chosen, points are evaluated starting with the end point at $t_2=t_1+\theta$. The end point for the segment, $t_2$, is chosen at a point which meets the criteria described above. In an embodiment, if an end point $t_2$ for a segment does not meet the criteria, a new candidate for $t_2$ is chosen as $t_2=t_2+$ one sample, until the limit $t_2>t_1+\rho$ is reached, and a new starting point for t1 is chosen. In alternate embodiments, other increments may also be used, for example, the next point, or a minimum segment length of 5 samples.

In an embodiment, the end point $t_2$ for the segment just defined is then used as the starting point $t_1$ for the next segment. In such an embodiment, only the new candidate for the end point of a segment need be tested to meet the criteria that user motion at the candidate end point is below a threshold.

Figure 6:
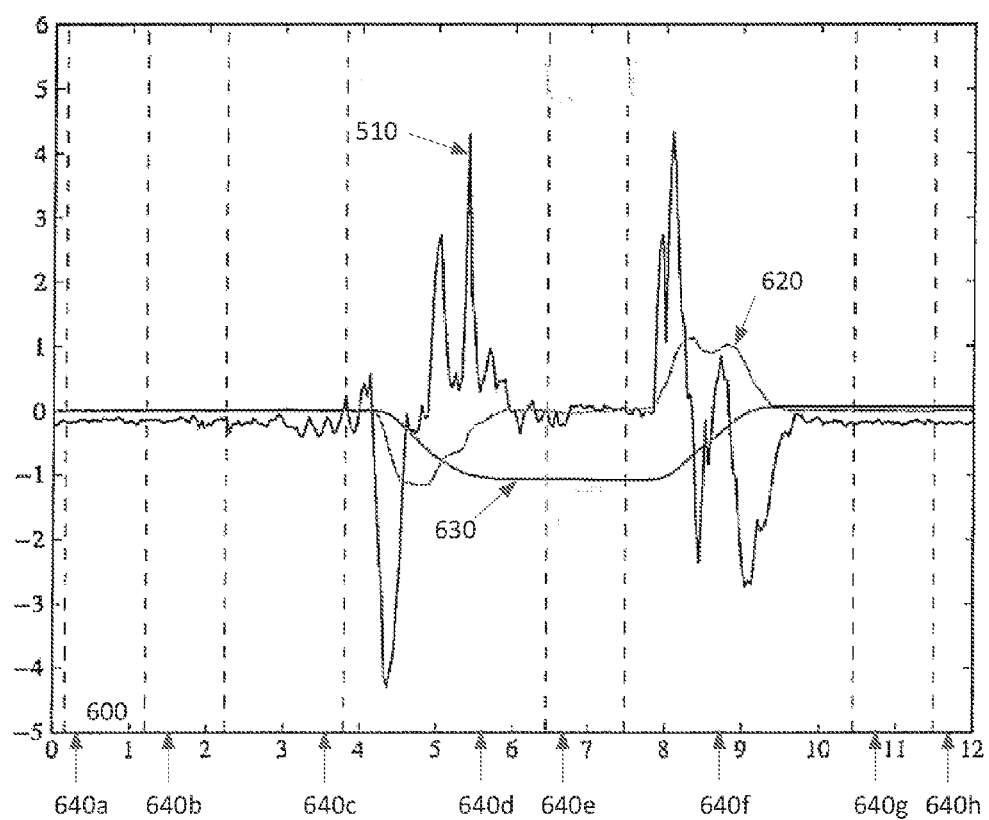
FIG. 6 is a graph of determining vertical displacement from accelerometer data according to an embodiment.

Returning to the graph of FIG. 6, the results of this segmentation process are shown. User motion is determined on a running basis as described previously herein from y-axis accelerometer samples. Initial segments 640a and 640b have user motion as shown by approximate vertical acceleration $a_v(t)$ 510, and uncorrected velocity $v_v(t)$, (as shown in 530 of FIG. 5) close to zero, and are of minimum time $\theta$ according to the criteria.

Examining segment 640d, an end point $t_2$ meeting the criteria is not found until the approximately six and one half second point, as user motion shown by approximate vertical acceleration $a_v(t)$ 510 does not return to near zero until the approximately six and one half second point. Segment 640f once more shows significant approximate vertical acceleration $a_v(t)$ 510, such that an end point $t_2$ meeting the criteria is not found until the approximately ten and a half seconds.

In an embodiment, the criteria that a minimal amount of user motion is present at the beginning and end points is determined by the following criteria:

vertical acceleration due to user motion at $t_1$ and $t_2$ is close to zero:

$$a_v(t_1) \approx 0 \text{ and } a_v(t_2) \approx 0$$

In an embodiment, vertical acceleration due to user motion $a_v(t)$ is considered close to zero when $a_v(t)$ is less than a threshold, for example, 0.1 meters/sec$^2$.

In another embodiment, the criteria that a minimal amount of user motion is present at the beginning and end points is instead determined by evaluating the bumpiness of vertical velocity $v_v(t)$ in the neighborhood of endpoint $t_2$.

Bumpiness is a measure of the degree of user motion over a neighboring period of time ending at the endpoint.

This bumpiness is defined by constructing a straight line from a point in the past, $v_v(t-\delta)$, where $\delta$ represents a point in time in the past, for example five seconds in the past, to the current value of the proposed endpoint $v_v(t_2)$ to estimate bumpiness in the neighborhood $\epsilon$ of $t_2$. This line, $f_l(k)$, at a point k is defined by:

$$f_l(k) = v_v(t_2) - k \frac{v_v(t_2) - v_v(t_2 - \delta)}{\delta}$$

In an embodiment, the value of $\delta$ is chosen to be, for example five seconds, $\delta=125$ points at 25 points per second.

Next, bumpiness B(t) at point $t_2$ is calculated as:

$$B(t_2) = \sqrt{\sum_{k=0}^{\varepsilon} (v_v(t_2-k) - f_l(k))^2}$$

where $\epsilon$ selects points in the recent past, for example 1 second, or $\epsilon=25$ points at 25 points per second, and bumpiness $B(t_2)$ sums the squares of the distances between vertical velocity points $v_v(t)$ and the point on the line $f_l(k)$. Thus the bumpiness $B(t_2)$ is a measure of user motion in the one second interval preceding point $t_2$.

If the bumpiness $B(t_2)$ is above a motion threshold, there cannot be a segment boundary at point $t_2$. The motion threshold is determined by the user vertical motion at point $t_2$. The motion threshold is set to a first predetermined value if the user vertical motion at end point $t_2$ is less than a predetermined motion limit. The motion threshold is set to a second predetermined value if the user vertical motion at end point $t_2$ is greater than or equal to the predetermined motion limit. The end point $t_2$ can be used as a segment boundary if the bumpiness $B(t_2)$ is not above the motion threshold.

In an embodiment, the predetermined motion limit is 7.5. The first predetermined value for the motion threshold is 3 and the second predetermined value for the motion threshold is 6.75. These values result from analyzing data captured over a number of sitting and standing sequences.

Figure 7:
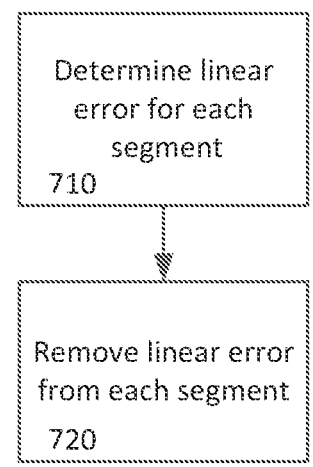
FIG. 7 is a flowchart detailing a method of correcting vertical velocity according to an embodiment.

Returning to FIG. 3, in step 350 the segments of vertical velocity determined in step 340 are corrected for the identified linear error. This process is shown in greater detail in FIG. 7.

By modeling the errors in the vertical velocity $v_v(t)$ as linear in nature as discussed previously herein, the corrected vertical velocity $\tilde{v}_v(t_2)$ at end point $t_2$ representing the end of a segment should be the same as the vertical velocity $v_v(t_1)$ at beginning point $t_1$ representing the beginning of the segment. In step 710, this linear error is determined by determining a linear equation for a line between the beginning vertical velocity $v_v(t_1)$ and ending vertical velocity $v_v(t_2)$ of the segment. In an embodiment, a slope m for a straight line between the beginning vertical velocity $v_v(t_1)$ and ending vertical velocity $v_v(t_2)$ of the segment is calculated as:

$$m = (v_v(t_2) - v_v(t_1))/n - 1$$

where n is the number of points in the segment from $t_1$ to $t_2$.

In step 720, this linear error is removed from each point in the segment by evaluating the linear equation just determined at a point t in the segment, and subtracting that value of the linear equation, which is the linear error, from the vertical velocity $v_v(t)$ to produce a point of corrected vertical velocity $\tilde{v}_v(t)$. In an embodiment, the corrected vertical velocity $\tilde{v}_v(t)$ for a point $t_i$ in the interval from $t_1$ to $t_2$ is:

$$\tilde{v}_v(t_i) = v_v(t_i) - (im/n-) \text{ for } i=0 \text{ to } n-1$$

where this is performed for each point, from $t_1$ to $t_2$, in the segment of vertical velocity, and for each of the segments of points of vertical velocity.

Comparing the graphs of FIG. 5 and FIG. 6, the difference between vertical velocity $v_v(t)$ 520 and corrected vertical velocity $\tilde{v}_v(t)$ 620 are readily apparent. In the period from zero to four seconds covering segments 640a, 640b, and 640c, vertical velocity $v_v(t)$ 520 has drifted negative from zero. In contrast, removing the linear error in each segment 640a through 640c, as shown in FIG. 6, corrected vertical velocity $\tilde{v}_v(t)$ in these segments remains at zero. The effect of this correction is also visible in the differences between vertical velocity $v_v(t)$ 520 and corrected vertical velocity $\tilde{v}_v(t)$ 620 in segments 640d and 640f.

Returning to FIG. 3, in step 360 vertical displacement $s_v(t)$ is determined using these corrected segments of points of vertical velocity $\tilde{v}_v(t)$ determined in step 350. A segment of points of vertical displacement $s_v(t)$ is determined for each corrected segment of points of vertical velocity $\tilde{v}_v(t)$. Once again, this step is performed using numerical integration of the corrected vertical velocity $\tilde{v}_v(t)$ to determine vertical displacement $s_v(t)$. In an embodiment, as described previously herein, by defining $\Delta t=1$, the process of numerical integration becomes a summing of the corrected vertical velocity $\tilde{v}_v(t)$ such that $$s_v(t) \approx \sum_{i=0}^{t} \tilde{v}_v(i)$$

where $\tilde{v}_v(i)$ is the corrected vertical velocity at a time i and $s_v(t)$ is the displacement at a time t.

In step 370, transitions between sitting and standing states are detected using the segments of points of vertical displacement $s_v(t)$. For each segment of points of vertical displacement $s_v(t)$, the vertical displacements of the beginning point of the segment $s_v(t_1)$ and the end point of the segment $s_v(t_2)$ are compared. If the difference between $s_v(t_1)$ and $s_v(t_2)$ is above a lower limit:

$$r_1 < |s_v(t_1) - s_v(t_2)|$$

where $r_1$ is the lower limit of the range, then a transition has been detected. If the vertical displacement $s_v(t_1) - s_v(t_2)$ is negative, a transition from standing to sitting has been detected. If the vertical displacement $s_v(t_1) - s_v(t_2)$ is positive, a transition from sitting to standing has been detected. In an embodiment, the lower limit $r_1$ is approximately 0.25 meters.

Placing a lower limit on the vertical displacement distinguishes between standing up, and for example standing on one's toes. Testing the vertical displacement at the beginning and end points of segments of points of vertical displacement also insures that the points at the beginning of the segment and the end of the segment are quiet; recall that as described previously herein, a quiet point is one where user motion and vertical velocity are close to zero.

Referring again to the graphs of FIG. 5 and FIG. 6, the effect of the correction mechanism described herein on vertical displacement and the resulting detection of transitions between sitting and standing states is illustrated.

In FIG. 5, vertical displacement $s_v(t)$ 530 drifts more and more negative. In comparison, in FIG. 6, vertical displacement $s_v(t)$ 630 based on corrected vertical velocity $\tilde{v}_v(t)$ decreases by approximately one meter in segment 640d; the user sat down, and a transition between standing and sitting states is detected. Similarly, in segment 640f, vertical displacement $s_v(t)$ 630 increases by approximately one meter; the user stood up, and a transition between sitting and standing states is detected.

The disclosed method and apparatus has been explained above with reference to several embodiments. Other embodiments will be apparent to those skilled in the art in light of this disclosure. Certain aspects of the described method and apparatus may readily be implemented using configurations other than those described in the embodiments above, or in conjunction with elements other than those described above. For example, although embodiments of the sensor device described herein discuss placement of the sensor device on the front of the torso, the sensor device can be placed on other parts of the body (e.g., back, head, or neck) as well.

As an example, while placing the sensor device on an extremity, such as on the arm, forearm, wrist, hand, leg, ankle, or foot does not support detecting transitions between sitting and standing, such sensor placement does allows the described method and apparatus to reliably determine vertical displacement in these extremities, such as raising of a hand, arm, leg, or foot.

Further, it should also be appreciated that the described method and apparatus can be implemented in numerous ways, including as a process, an apparatus, or a system. The methods described herein may be implemented by program instructions for instructing a processor to perform such methods, and such instructions recorded on a non-transitory computer readable storage medium such as a hard disk drive, floppy disk, optical disc such as a compact disc (CD) or digital versatile disc (DVD), flash memory, etc., or a computer network wherein the program instructions are sent over optical or electronic communication links. It should be noted that the order of the steps of the methods described herein may be altered and still be within the scope of the disclosure.

It is to be understood that the examples given are for illustrative purposes only and may be extended to other implementations and embodiments with different conventions and techniques. While a number of embodiments are described, there is no intent to limit the disclosure to the embodiment(s) disclosed herein. On the contrary, the intent is to cover all alternatives, modifications, and equivalents apparent to those familiar with the art.

In the foregoing specification, the invention is described with reference to specific embodiments thereof, but those skilled in the art will recognize that the invention is not limited thereto. Various features and aspects of the above-described invention may be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of detecting a user transition between sitting and standing states comprising:

capturing, by a tri-axial accelerometer attached to a user, a plurality of points of accelerometer data for at least first, second and third axes over a period of time, determining, by a microprocessor, a plurality of points of approximate acceleration magnitude, which comprises determining, at each of the plurality of points of accelerometer data, a difference between an acceleration vector magnitude and a value for an acceleration due to gravity, wherein the acceleration vector magnitude is a vector magnitude of accelerometer data for the first, second, and third axes at a point in time, determining, by the microprocessor, a plurality of points of velocity vector magnitude from the plurality of points of approximate acceleration magnitude, determining, by the microprocessor, a segment comprising selecting a first point in time of the velocity vector magnitude and a second point in time of the velocity vector magnitude that satisfy at least a condition that a length of the segment is within a predetermined range and a condition that the first point in time of the velocity vector magnitude and the second point in time of the velocity vector magnitude are below a threshold of user motion, wherein the first point in time and the second point in time correspond to beginning and end points of the segment, respectively, for each of the first and second points in time:
setting, by the microprocessor, the threshold of user motion to be a first predetermined value if a user motion at the respective point is less than a predetermined motion limit,
setting, by the microprocessor, the threshold of user motion to be a second predetermined value if the user motion at the respective point is greater than or equal to the predetermined motion limit, and
wherein determining the condition that the first point in time of the velocity vector magnitude and the second point in time of the velocity vector magnitude are below the threshold of user motion is determining, by the microprocessor, that a degree of the user motion over a neighboring period of time ending at the respective point is less than the set threshold of user motion, correcting, by the microprocessor, the plurality of points of velocity vector magnitude within the segment, determining, by the microprocessor, a plurality of points of vertical displacement for the corrected plurality of points of velocity vector magnitude, and detecting, by the microprocessor, that the user has transitioned between the sitting and standing states from a comparison of a vertical displacement at the first point in time and a vertical displacement at the second point in time.

2. The method of claim 1 further comprising:
determining, by the microprocessor, a running average of a magnitude of each of the plurality of points of accelerometer data, and
periodically updating, by the microprocessor, the value for the acceleration due to gravity using the running average of the magnitude of each of the plurality of points of accelerometer data.

3. The method of claim 1 wherein selecting the first point in time and the second point in time additionally satisfies a condition that the plurality of points of the approximate acceleration magnitude at the first and second points in time are less than an acceleration threshold.

4. The method of claim 1 wherein correcting the plurality of points of velocity vector magnitude within the segment comprises:
determining, by the microprocessor, a linear error for the plurality of points of velocity vector magnitude within the segment, and
removing, by the microprocessor, the linear error from the plurality of points of velocity vector magnitude.

5. The method of claim 1 where detecting that the user has transitioned between the sitting and standing states comprises:
determining, by the microprocessor, a change in displacement between the vertical displacement at the first point in time and the vertical displacement at the second point in time,
detecting, by the microprocessor, that the user has transitioned between the sitting state to the standing state when the change in displacement is positive and greater than a predefined limit, and
detecting, by the microprocessor, that the user has transitioned between the standing state to the sitting state when the change in displacement is negative and less than the predefined limit.

6. The method of claim 1 wherein the degree of the user motion over a neighboring period of time ending at the respective point is a bumpiness value of points of the velocity vector magnitude in the neighboring period of time ending at the respective point.

7. An apparatus for detecting a user transition between sitting and standing states comprising:
a tri-axial accelerometer configured to be attached to a user and to capture a plurality of points of accelerometer data over a period of time for first, second, and third axes, and
a microprocessor, coupled to the tri-axial accelerometer, the microprocessor configured to:
determine a plurality of points of approximate acceleration magnitude by determining, at each of the plurality of points of accelerometer data, a difference between an acceleration vector magnitude and a value for an acceleration due to gravity, wherein the acceleration vector magnitude is a vector magnitude of accelerometer data for the first, second, and third axes at a point in time,
determine a plurality of points of velocity vector magnitude from the plurality of points of approximate acceleration magnitude,
determine a segment by,
selecting a first point in time of the velocity vector magnitude and a second point in time of the velocity vector magnitude that satisfy at least a condition that a length of the segment is within a predetermined range and a condition that the first point in time of the velocity vector magnitude and the second point in time of the velocity vector magnitude are below a threshold of user motion, wherein the first point in time and the second point in time correspond to beginning and end points of the segment, respectively, and
determining, based on a motion threshold, that a minimal amount of the user motion is present at the first point in time and the second point in time by being configured to, for each of the first point in time and the second point in time: set the threshold of user motion to be a first predetermined value if a user motion at the respective point is less than a predetermined motion limit, set the threshold of user motion to be a second predetermined value if the user motion at the respective point is greater than or equal to the predetermined motion limit, and determine that a degree of the user motion over a neighboring period of time ending at the respective point is less than the set threshold of user motion, correct the plurality of points of velocity vector magnitude within the segment, determine a plurality of points of vertical displacement for the corrected plurality of points of velocity vector magnitude, and detect the user transition between the sitting and standing states from a comparison of a vertical displacement at the first point in time and a vertical displacement at the second point in time.

8. The apparatus of claim 7 where the microprocessor is further configured to:

determine a running average of a magnitude of each of the plurality of points of accelerometer data, and periodically update the value for the acceleration due to gravity using the running average of the magnitude of each of the plurality of points of accelerometer data.

9. The apparatus of claim 7 wherein selecting the first point in time and the second point in time additionally satisfies a condition that the plurality of points of the approximate acceleration magnitude at the first and second points in time are less than an acceleration threshold.

10. The apparatus of claim 7 wherein the microprocessor is configured to correct the points of velocity vector magnitude within the segment by being configured to:

determine a linear error for the plurality of points of velocity vector magnitude within the segment, and remove the linear error from the plurality of points of velocity vector magnitude.

11. The apparatus of claim 7 where the microprocessor is configured to detect that the user has transitioned between the sitting and standing states by being configured to:

determine a change in displacement between the vertical displacement at the first point in time and the vertical displacement at the second point in time, detecting that the user has transitioned between the sitting state to the standing state when the change in vertical displacement is positive and greater than a predefined limit, and detecting that the user has transitioned between the standing state to the sitting state when the change in vertical displacement is negative and less than the predefined limit.

12. The apparatus of claim 7 wherein the degree of the user motion over a neighboring period of time ending at the respective point is a bumpiness value of points of the velocity vector magnitude in neighboring period of timeending at the respective point.

* * * * *